United States Patent [19]
Zdeb

[11] Patent Number: 5,306,257
[45] Date of Patent: Apr. 26, 1994

[54] DRUG INFUSER

[75] Inventor: Brian D. Zdeb, Round Lake, Ill.

[73] Assignee: Prime Medical Products, Inc., Round Lake Park, Ill.

[21] Appl. No.: 878,364

[22] Filed: May 4, 1992

[51] Int. Cl.$^5$ ............................................. A61M 37/00
[52] U.S. Cl. ..................................... 604/131; 604/251
[58] Field of Search ............... 604/141, 132, 131, 251, 604/256

[56] References Cited

U.S. PATENT DOCUMENTS

| | | |
|---|---|---|
| 3,032,037 | 5/1962 | Huber . |
| 3,412,906 | 11/1968 | Dinger . |
| 3,468,308 | 9/1969 | Bierman . |
| 3,486,539 | 12/1969 | Jacuzzi . |
| 3,506,005 | 4/1970 | Gilio et al. . |
| 3,731,681 | 5/1973 | Blackshear et al. . |
| 3,889,675 | 6/1975 | Stewart ................................. 604/34 |
| 3,991,763 | 11/1976 | Genese . |
| 4,112,947 | 9/1978 | Nehring . |
| 4,121,584 | 10/1978 | Turner et al. . |
| 4,140,117 | 2/1979 | Buckles et al. . |
| 4,204,538 | 5/1980 | Cannon . |
| 4,230,244 | 10/1980 | Zissimopoulos . |
| 4,248,223 | 2/1981 | Turner et al. . |
| 4,261,356 | 4/1981 | Turner et al. . |
| 4,299,220 | 11/1981 | Dorman . |
| 4,299,222 | 11/1981 | Eckenhoff . |
| 4,318,400 | 3/1982 | Peery et al. . |
| 4,337,769 | 7/1982 | Olson ................................. 604/251 |
| 4,419,096 | 12/1983 | Leeper et al. . |
| 4,437,590 | 3/1992 | LaBruna . |
| 4,496,343 | 1/1985 | Prosl et al. . |
| 4,581,018 | 4/1986 | Jassawalla et al. . |
| 4,604,090 | 8/1986 | Reinicke . |
| 4,722,732 | 2/1988 | Martin . |
| 4,723,947 | 2/1988 | Konopka . |
| 4,758,224 | 7/1988 | Siposs ................................. 604/297 |
| 4,820,273 | 4/1989 | Reinicke ..................... 128/DIG. 12 |
| 4,898,582 | 2/1990 | Faste . |
| 4,898,584 | 2/1990 | Borsanyi et al. . |
| 4,902,278 | 2/1990 | Maget et al. . |
| 4,915,693 | 4/1990 | Hessel . |
| 4,925,451 | 5/1990 | Amendolia . |
| 4,931,050 | 6/1990 | Idriss . |
| 4,938,751 | 7/1990 | Leeper et al. . |
| 4,968,301 | 11/1990 | di Palma et al. . |
| 4,969,873 | 11/1990 | Steinbach et al. . |
| 4,995,864 | 2/1991 | Bartholomew et al. . |
| 4,998,918 | 3/1991 | Mimura . |
| 5,011,477 | 4/1991 | Winchell et al. . |
| 5,024,663 | 6/1991 | Yum . |
| 5,045,064 | 9/1991 | Idriss ................................. 604/132 |
| 5,167,631 | 12/1992 | Thompson et al. ................. 604/132 |
| 5,171,301 | 12/1992 | Vanderveen ......................... 604/132 |

FOREIGN PATENT DOCUMENTS

| | | |
|---|---|---|
| 0270500 | 6/1988 | European Pat. Off. . |
| 0307069 | 3/1989 | European Pat. Off. . |
| 0408256A1 | 1/1991 | European Pat. Off. . |
| 86/01597 | 2/1987 | PCT Int'l Appl. . |
| 1454310 | 11/1976 | United Kingdom ................. 604/132 |

Primary Examiner—Paul J. Hirsch
Attorney, Agent, or Firm—Leydig, Voit & Mayer

[57] ABSTRACT

An infuser apparatus for the delivery of fluid at accurate and controlled rates of flow comprising a housing, a deformable member, inlet means and outlet means. Fluid is introduced through the inlet means forcing the deformable member to bend away from its normal position and to generate a pressure force against the fluid introduced. When the outlet means is opened, the fluid is expelled by means of the deformable member returning to its normal position. The infuser apparatus may expel the fluid at either a constant or at a varied and controlled rate depending on the configuration of the deformable member. Further, multiple infusers may be coupled together in a fluid delivery system.

47 Claims, 9 Drawing Sheets

DRUG INFUSER

FIELD OF THE INVENTION

The present invention relates generally to self-propelled fluid delivery devices and specifically to controlled discharge drug infusers.

BACKGROUND OF THE INVENTION

Numerous devices have been utilized in the past for infusing drugs or other liquid solutions to persons requiring extended exposure to such solutions. In order to avoid the operational complexities associated with externally powered pumping devices, a great deal of inventive effort has been focused on devices having internally powered mechanical delivery mechanisms.

One concept that has received considerable attention involves the use of a deformable bladder such as that disclosed in U.S. Pat. No. 4,419,096 to Leeper et al. As explained in Leeper, however, a fundamental operational difficulty encountered by the use of a deformable bladder is non-uniformity of operation resulting in a pressure spike near the end of the fluid dispersion cycle. This pressure spike results in a corresponding surge in fluid flow to the patient which is generally undesirable. Leeper addresses this problem by inclusion within the bladder of means to maintain the bladder in a slightly bulbar configuration. The detriment associated with this configuration is, of course, that the medicinal fluid is not completely expelled from the bladder and is therefore wasted. A number of other patents have disclosed configurations utilizing bladders but none appear to have the capability of completely delivering the stored contents at a controlled pressure and flow rate.

To avoid the inherent problems of non-uniform delivery associated with devices such as Leeper, wherein flow is initiated through the collapse of an elastic bladder, a number of alternative concepts have emerged utilizing various driving means to expel the fluid contained in the infusion device. These include inter alia, the spring loaded piston of Turner et al. U.S. Pat. No. 4,248,223, the osmotic pump disclosed in Faste U.S. Pat. No. 4,898,582 and the introduction of pressurization means to aid in the collapse of a rolling diaphragm as disclosed in LaBruna U.S. Pat. No. 4,437,590. Several devices have attempted to avoid the need for a separate driving means to expel the fluid from the apparatus through use of stretched elastomeric membranes. Elastically driven devices are exemplified in Kriesel U.S. Pat. No. 5,019,047 and di Palma et al. U.S. Pat. No. 4,968,301. Kriesel discloses an apparatus for infusing medicinal fluids into a patient at specific rates over extended periods of time. The driving force to expel the fluid contained in the apparatus is provided by the relief of internal stresses created through the stretching of an elastically deformable membrane. The flow-rate of the fluid thereby expelled is controlled by a thin fluid permeable member 26. Similarly, di Palma also utilizes the force generated from an elastically stretched membrane to expel the medicinal fluid.

It is noteworthy that in relying on force generated by a stretched membrane, both Kriesel and di Palma operate in a manner which is fundamentally different from the present invention. While the membranes in Kriesel and di Palma must be stretched, thereby placing significant stresses on components within the infuser and giving rise to enhanced potential for malfunction and breakage, force relied on in the present invention is primarily the bending force derived from a bendably deformable member.

Despite the existence of infusion devices which are capable of delivering fluids at a specific rate over an extended period of time, there remains a need for a simple infusion device which overcomes the deficiency of those devices which are dependent on the use of stretched elastic members, without resorting to external control methods such as those commonly taught and utilized in the art. Specifically, there is a need for a simple, effective infusion device which does not place great stress on the infuser components due to stretching of a diaphragm member. There is also a need for a simple device which is capable of delivering fluids at either constant or variable controlled flow rates without relying on external flow control mechanisms and which may be coupled to similar devices to deliver a plurality of fluids either simultaneously or at staged intervals.

OBJECTS OF THE PRESENT INVENTION

The principal object of the present invention is to provide a device for the controlled infusion of fluids which overcomes the complexities and deficiencies of the prior art. Accordingly, it is a primary object of the present invention to provide an infusion device for the delivery of drugs or other fluids at a controlled rate of flow substantially by relief of the internal bending strain of a deformable member, thereby eliminating the need for the use of external forces or rigid driving members. It is yet a further object of the present invention to provide an infusion device providing a controlled multistage output through the use of deformable members having portions of varying rigidity, thereby imparting different forces to the fluid being delivered at different stages of the deformable member recovery. It is still a further object of the present invention to provide a system for the delivery of drugs or other fluids through a networking of infuser apparatuses with the option of combining infusing apparatuses with complimentary staged delivery characteristics.

SUMMARY OF THE INVENTION

The present invention provides an infuser apparatus for the delivery of fluids at a controlled rate. The infuser of the present invention comprises a housing made up of two sections. The two housing sections are joined together to form a chamber. Fluid may be introduced into this chamber by means of fluid inlet and outlet means located in the housing body.

In the present invention, a deformable member is located inside the enclosed chamber. The edges of the deformable member are sandwiched between the housing sections, thereby securing the deformable member in place. The disposition of the deformable member within the chamber is such that it will normally lie against the inner surface of the housing section in which the fluid inlet and outlet means are located.

As fluid is introduced into the chamber through the fluid inlet means, the deformable member bends away from its normal position against the chamber's inner surface. This bending action takes place substantially without a stretching of the deformable member.

A pressure force is exerted against the fluid introduced as the deformable member seeks to return to its original disposition against the inner surface of the chamber through relief of the bending strain caused by the filling operation.

Once the fluid filling procedure is terminated and the fluid outlet means are opened, the fluid will be discharged. The rate of discharge is determined by the force exerted by the deformable member as it returns to its pre-bent position.

The fluid expulsion force produced by the return of the deformable member to its original position is a function of the rigidity of that portion of the deformable member subjected to bending strain. A more rigid deformable member will exert a greater expulsion force than a less rigid member. Accordingly, the present invention may utilize deformable members of varying rigidity to obtain varying expulsion forces.

The present invention is also adaptable for use with additional flow control means. Such flow control means may be located downstream from the infuser and serve to provide additional flow control over that achievable through use of the infuser alone. Finally, due to the pressure based flow control technique utilized in the present invention, multiple infusers may be coupled to a common header to deliver a plurality of fluids at varying flow rates.

BRIEF DESCRIPTION OF THE DRAWINGS

FIG. 11A shows the valve in the closed position and the unlocking mechanism partially inserted and in sealing engagement with the valve. FIG. 11B shows the unlocking mechanism fully inserted into the valve and the valve in the open position.

While the invention will be described and disclosed in connection with certain preferred embodiments and procedures, it is not intended to limit the invention to those specific embodiments. Rather it is intended to cover all such alternative embodiments and modifications as fall within the spirit and scope of the invention.

DETAILED DESCRIPTION OF THE PREFERRED EMBODIMENTS

Figure 1:
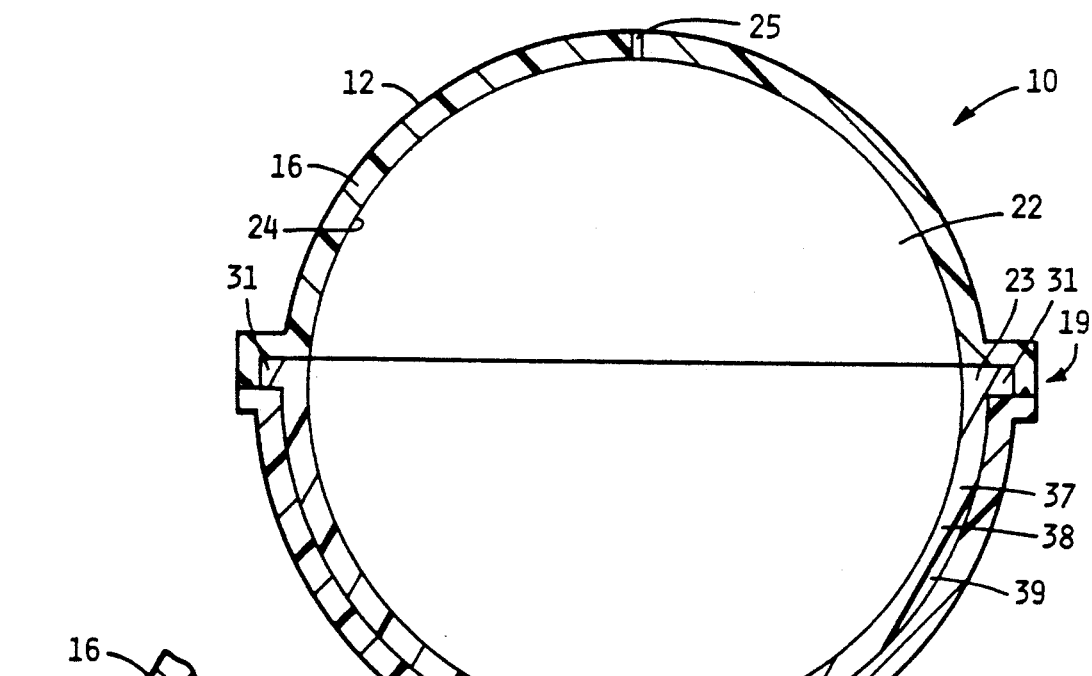
FIG. 1 is a cross section of one embodiment of the drug infuser of the present invention prior to introduction of fluid.
Figure 3:
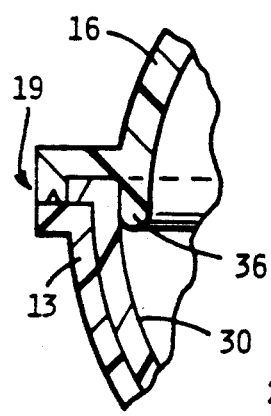
FIG. 3 is a cross section of an illustrative sealing arrangement for use in the drug infuser of the present invention.
Figure 2:
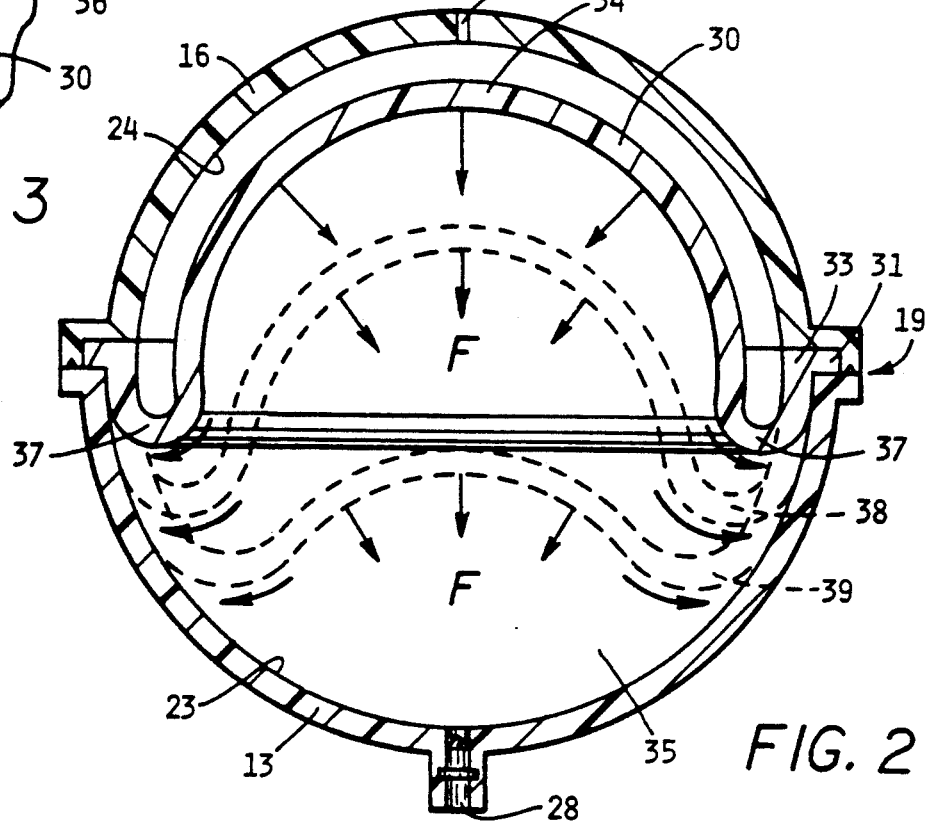
FIG. 2 is a cross section of the drug infuser of FIG. 1 filled to various levels.

Referring now to FIGS. 1-3, the controlled discharge drug infuser device 10 of the present invention includes a housing 12 comprising a first portion 13 and a second portion 16. First portion 13 and second portion 16 may be joined at interface 19 by sealing means, including, for example, ultrasonic welding, chemical adhesives or mechanical clamping devices (not shown) such as are well known to those skilled in the art. As will be discussed in greater detail below, the present invention contemplates that the first and second portions 13, 16 may be of various geometric configurations.

The first and second portions 13, 16 combine to form an inner chamber 22 having a first inner surface 23 and a second inner surface 24. Inner chamber 22 communicates with the atmosphere by means of a vent orifice 25. Inner chamber 22 is also provided with fluid inlet/outlet means 28 as described in greater detail below.

In the preferred embodiment of the invention, a deformable member 30 is disposed within the inner chamber 22 so as to form a fluid tight movable barrier between the inlet/outlet means 28 and the second inner surface 24. The fluid tight barrier could, however, also be achieved by separate means such as through use of a prefilled insertable bag-like member (not shown).

While the present invention is not limited to any specific disposition of the deformable member 30 within the inner chamber 22, in the illustrated embodiment, the periphery 31 of deformable member 30 is sandwiched in between the first and second members 13, 16 of the housing 12. Engagement of the periphery 31 of deformable member 30 with the housing 12 defines a non-movable foot portion 33 around the perimeter of inner chamber 22 at the junction 19 of first and second portions 13, 16 of the housing 12. As shown in FIG. 2, the non-movable foot portion 33 remains substantially undeformed as the interior of the deformable member 30 is bent towards or away from the vent orifice 25 as inner chamber 22 is filled with liquid or as liquid is expelled.

In the illustrated embodiment shown in FIG. 1, the deformable member 30 is of uniform thickness and is normally disposed (i.e., when the inner chamber 22 is empty) in substantially contacting relation with the first inner surface 23. A fluid such as a medicinal agent may be introduced into the inlet/outlet means 28 to fill chamber 22. Filling chamber 22 forces the deformable member 30 to bend away from the first inner surface 23. As illustrated in FIG. 2, this bending action is initiated at the center 34 of deformable member 30 and proceeds toward the perimeter 31 of deformable member 30 as fluid is introduced. As the fluid forces the deformable member 30 away from the inner surface 23, a fluid storage area 35 is defined between the deformable member 30 and the inner surface 23 of the first portion 13 of housing 12. The fluid which is introduced into the fluid storage area 35 is thus bounded by the deformable member 30 which functions as a fluid-tight barrier between the inner surface 23 and inner surface 24. As will be recognized by those skilled in the art, as fluid enters inner chamber 22, air must be expelled at an equivalent rate in order to maintain pressure equilibrium. This air expulsion is effected by means of vent orifice 25. Similarly, as fluid is removed from inner chamber 22, vent orifice 25 serves to admit air into the space formerly filled by fluid thereby substantially avoiding the creation of a vacuum.

FIG. 3 illustrates an embodiment of the seal between first and second housing portions 13, 16. In the sealing embodiment illustrated in FIG. 3, second housing section 16 is provided with an extension member 36 which serves to hold the non-movable foot portion 33 in place following the joinder of first housing section 13 to second housing section 16. As will be readily recognized by those skilled in the art, the securement of foot portion 33 between first and second housing sections 13, 16 may be effected by numerous alternative sealing arrangements. Accordingly, the present invention is not limited to the specific sealing arrangement illustrated in FIG. 3.

In the illustrated embodiment of the invention as shown in FIG. 2, the deformable member 30 is in direct contact with the fluid housed within infuser 10. The present invention may, however, incorporate a flexible barrier element or film (not shown) disposed between the fluid and the deformable member 30, thereby preventing direct contact between the fluid and the deformable member. In such an embodiment, the barrier element utilized will preferably be composed of a resilient biocompatible material capable of moving in conjunction with the deformable member 30. As will be recognized, the use of a biocompatible barrier element allows a greater range of materials to be used in the construction of the deformable member 30, since the potential for contamination of the fluid by deformable member 30 is eliminated.

Following the introduction of fluid into fluid storage area 35 and the resultant bending of the deformable member 30 to its bent position, as shown in FIG. 2, inlet/outlet means 28 may be sealed, thereby serving to store the fluid within the infuser 10. When the fluid housed between deformable member 30 and first inner surface 23 is to be used, inlet/outlet means 28 is opened and the fluid is expelled by means of a force F generated by the recovery of bending strain in the deformable member 30.

According to one aspect of the invention, the deformable member 30 may be disposed within the infuser 10 in a manner such that the deformable member 30 is disposed in a state of compressive stress prior to the introduction of fluid into the fluid storage area 35. That is, deformable member 30 is disposed within infuser 10 such that the deformable member 30 does not achieve a state of complete relaxation upon coming to rest against first inner surface 23. This preloading of the deformable member 30 permits virtually complete and steady expulsion of the fluid housed within the infuser 10. Conversely, infusers in which the deformable member is allowed to become completely relaxed prior to contacting first inner surface 23 may not provide complete expulsion of the fluids contained therein and may experience variations in pressure and flow rate during the final stages of relaxation.

In accordance with an important aspect of the present invention, the deformable member 30 does not stretch to a significant degree as the medicinal fluid enters the fluid storage means 35. The force F generated by the deformable member 30 is primarily a function of the bending strain recovery of deformable member 30 rather than the stretching of the deformable member 30. Hence, while some stretching may occur, the present invention represents a fundamental departure from previous devices which have relied on the use of stretched elastomeric diaphragms to generate a fluid driving force.

The generation of the fluid expulsion force in the present invention is best illustrated by reference to FIG. 2. In FIG. 2, the deformable member 30 is illustrated with the infuser 10 filled to various levels. When the infuser 10 of the present invention is substantially filled, the fluid expulsion force F is controlled by relief of the bending strain at the outermost bendable portion 37 of deformable member 30. As portion 37 returns to its natural contacting relation with first inner surface 23, the bendable member 30 is essentially pulled down towards inlet/outlet means 28, thereby giving rise to the fluid expulsion force F.

As deformable member 30 is pulled down, the bend shifts away from the periphery of the deformable member 30 and towards the center 34. After some fluid has been expelled, the bend which serves to pull deformable member 30 down towards the first inner surface 23 is located at portion 38 of deformable member 30. It will be recognized that at this stage of expulsion, portion 37 no longer affects the fluid expulsion force F, as the bending strains within that portion have been substantially relieved.

As illustrated in FIG. 2, at still a later stage of the fluid expulsion, the bend is located at portion 39 of deformable member 30. At this stage, neither portions 37 nor 38 play a role in generating the expulsion force F.

Since the fluid expulsion force F is generated by the gradual unbending of deformable member 30 as described above, the magnitude of the expulsion force F can be varied through control of the bending recovery force operating at each stage of recovery. Control of the bending recovery force may be effected through control of the rigidity of the deformable member 30.

Figure 4:
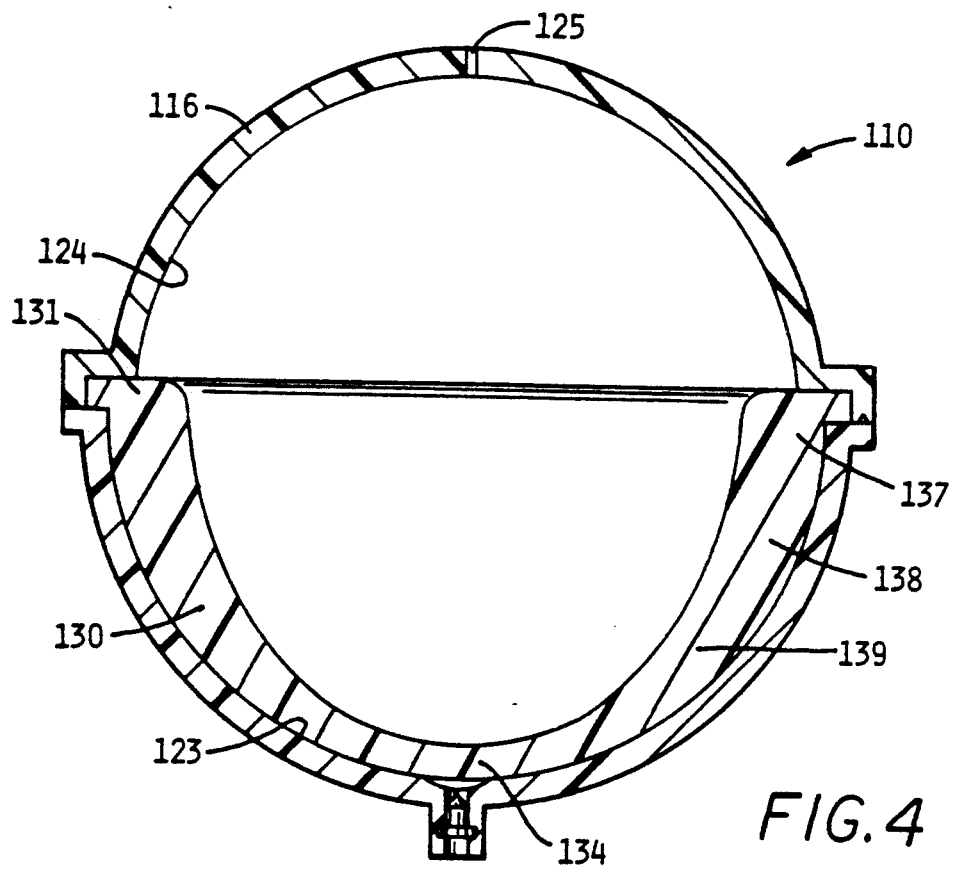
FIG. 4 is a cross section of an alternative embodiment of the drug infuser of the present invention prior to introduction of fluid.
Figure 5:
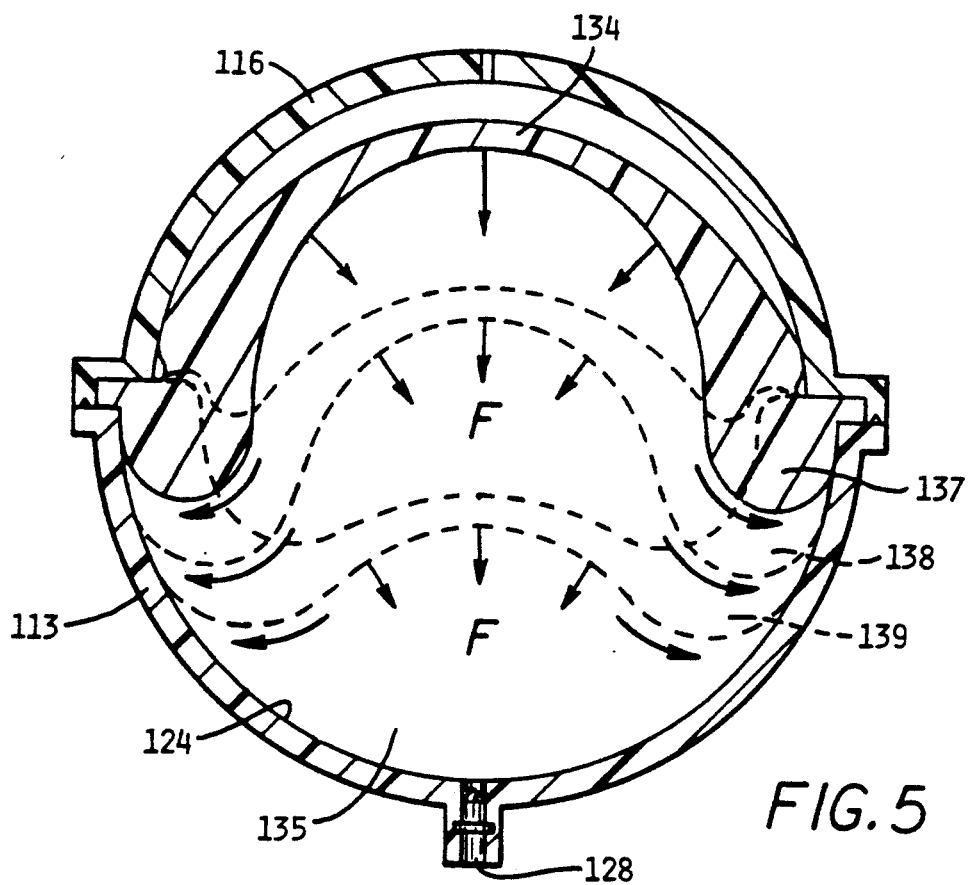
FIG. 5 is a cross section of the drug infuser of FIG. 4 filled to various levels.

One method of controlling the rigidity of the deformable member is illustrated in FIGS. 4 and 5. The deformable member 130 of the embodiment of the invention illustrated in FIGS. 4 and 5 is of a non-uniform thickness. That is, the perimeter 137 is substantially thicker, and hence more rigid, than the center section 134. Accordingly, the fluid expulsion force F will vary as different portions of deformable member 130 return to their prefilled contacting relation with first inner surface 123. Specifically, since the periphery 137 of the deformable member 130 is thicker than the center portion 134, the fluid expulsion force F generated during the initial stages of fluid discharge will be greater than the expulsion force generated at the final stages of discharge. Consequently, the flow rate will vary accordingly. That is, the rate of discharge will be relatively high during the initial stages of expulsion and will decrease to a lower rate as the bending strain in deformable member 130 is relieved.

Referring to FIG. 5, when the infuser 110 is substantially filled, the controlling bend in the deformable member is located at the peripheral portion 137 of bendable member 130. Due to the extreme thickness (and hence high rigidity) of peripheral portion 137, a relatively high pulling force is generated as peripheral portion 137 returns to its normal relaxed position. Thus, the fluid expulsion force F will be correspondingly great.

At a later stage of discharge, the bend has moved to portion 138 of deformable member 130. As may be seen, portion 138 is thinner and hence less rigid than portion 137. Accordingly, the pulling force generated as portion 138 returns to its normal relaxed position will be less than that produced during the earlier stages of fluid discharge. Thus, the fluid expulsion force F and resultant flow rate will also be lower than the pulling force and flow rate generated as peripheral portion 137 returns to its normal relaxed position.

At still a later stage of discharge, the controlling bend has moved to portion 139 of deformable member 130. Since portion 139 is thinner than portions 137 and 138 the fluid expulsion force produced by elimination of the bending strain at portion 139 will be lower than that produced during the previous stages of expulsion.

Figure 6:
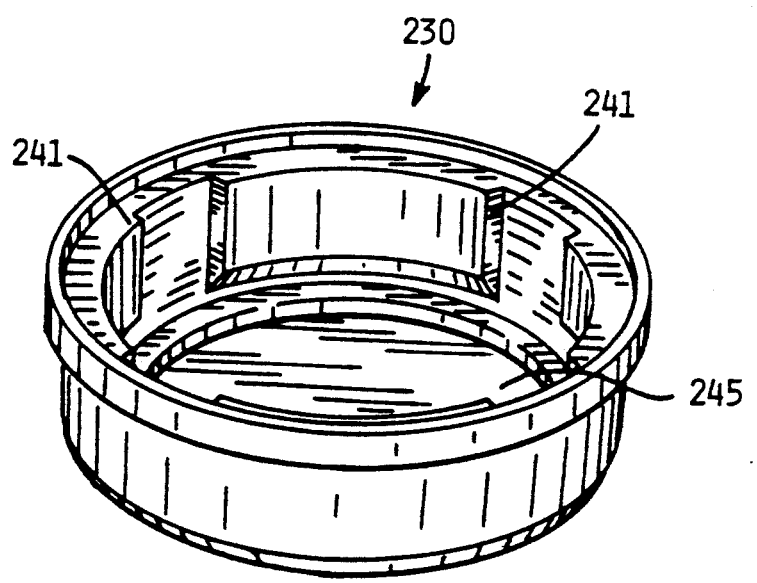
FIG. 6 is a perspective view of a ribbed deformable member for use in the infuser of the present invention.

It will be appreciated by those skilled in the art that the rigidity of deformable member 30 or 130 may be controlled by methods other than through a variation in thickness. For example, as illustrated in FIG. 6, the deformable member may incorporate the use of raised ribs 241 disposed over various sections of the deformable member. A controlled expulsion force may thereby be generated while substantially reducing the amount of material needed to construct deformable member 230. While not illustrated, other alternatives would also fall within the scope of the present invention. For example, if the fluid tight seal between first inner surface 23 and second inner surface 24 is maintained by a deformable member other than the bendable member 30, 130, the deformable member 30, 130 could actually incorporate perforations thereby reducing manufacturing materials requirements even further.

Figure 7:
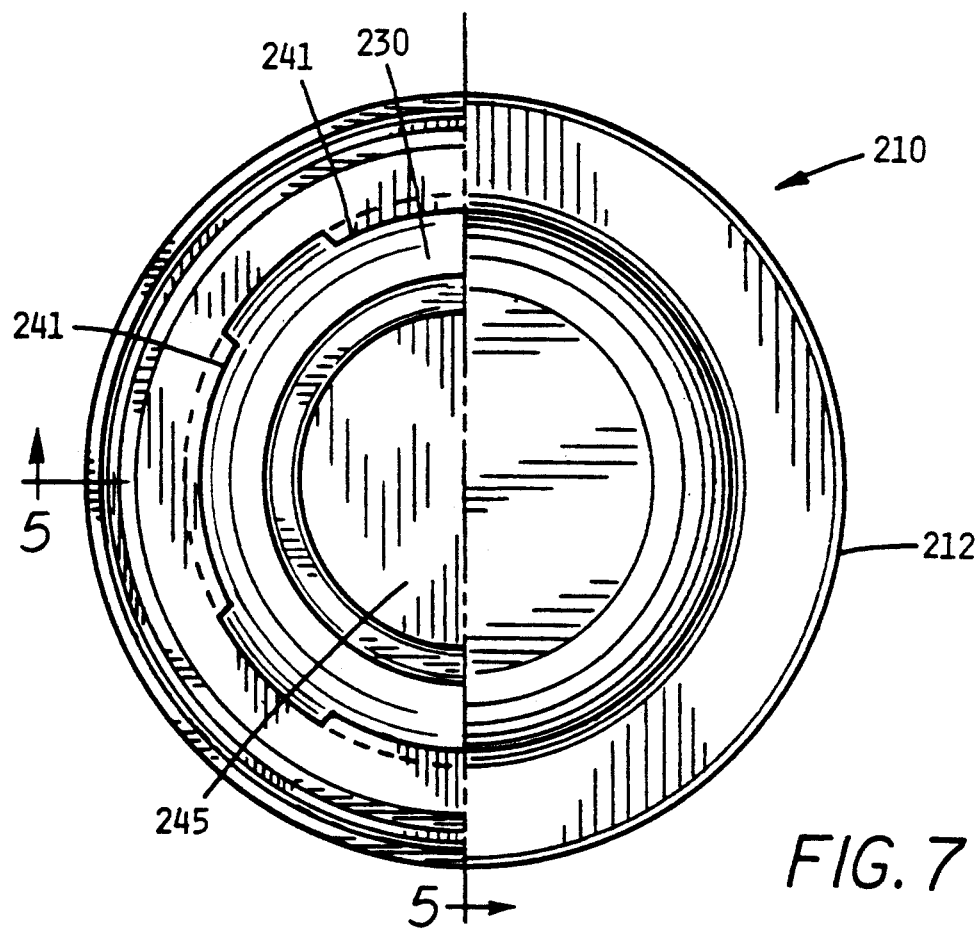
FIG. 7 is a top view of an embodiment of the infuser of the present invention incorporating the ribbed member illustrated in FIG. 6.
Figure 8:
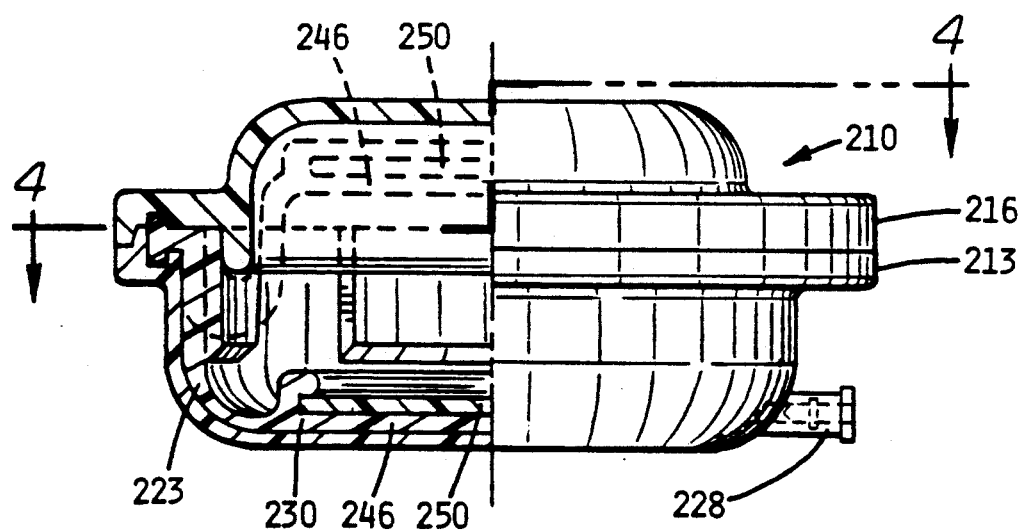
FIG. 8 is a side view of one embodiment of the infuser of the present invention incorporating the ribbed member illustrated in FIG. 6 taken along line 8—8 of FIG. 7.

An infuser 210 incorporating the ribbed member 230 of FIG. 6 is illustrated in top view and side view in FIGS. 7 and 8, respectively. As may be seen, the infuser apparatus 210 illustrated in FIGS. 7 and 8 is of a substantially cylindrical configuration. Thus, as previously indicated, the present invention is adaptable to numerous geometries including, for example, the spherical geometry illustrated in FIG. 1, the cylindrical geometry illustrated in FIG. 8 and a substantially rectangular configuration illustrated in FIG. 10. Notably, as discussed below, the discharge control for all geometric configurations is essentially identical to that described above with relation to the spherical design.

In the non-spherical embodiment of the present invention illustrated in FIGS. 7 and 8, the center section 245 of deformable member 230 is substantially rigid. That is, the center section 245 will maintain substantially the same planar configuration as fluid is introduced into, or expelled from, the infuser 210. As is apparent, the substantially rigid center section 245 permits a contacting relation to be achieved between deformable member 230 and the flat portion 246 of first inner surface 223. The contacting relation is desired to effect a substantially complete discharge of the stored fluid. In the embodiment illustrated in FIG. 8, the substantial rigidity of the center portion 245 of deformable member 230 is achieved by means of a plastic disk 250. While the disk 250 is shown in FIG. 8 as being disposed on the ventilation side of deformable member 230, a disk composed of an appropriate biocompatible material could also be disposed on the fluid side of the deformable member Likewise, the requisite rigidity in the center of the deformable member 230 may be achieved through means other than a plastic disk such as by thickening the center section of the deformable member 230 or through use of alternative reinforcing elements.

Regardless of the geometric embodiment of the invention, the deformable member is preferably formed from a resilient material which is biocompatible with the human body and likewise compatible with the fluid to be stored and discharged. For example, heat cured man made synthetic rubber such as synthetic silicon rubber or natural latex rubber or like material may be used as can non-heat cured thermoplastic elastomers such as SANTOPRENE thermoplastic rubber which is produced by the Monsanto Company and marketed by Advanced Elastomer Systems Inc.

Similarly, the housing of the infuser 10 is preferably composed of a biocompatible thermoplastic material such as, for example, polyacrylates ("acrylic"), polypropylenes, or polycarbonates. In the preferred embodiment, the material forming the housing will be of sufficient strength and heat resistance to permit the infuser apparatus 10 to be factory prefilled and autoclaved prior to distribution for individual use.

Figure 9A:
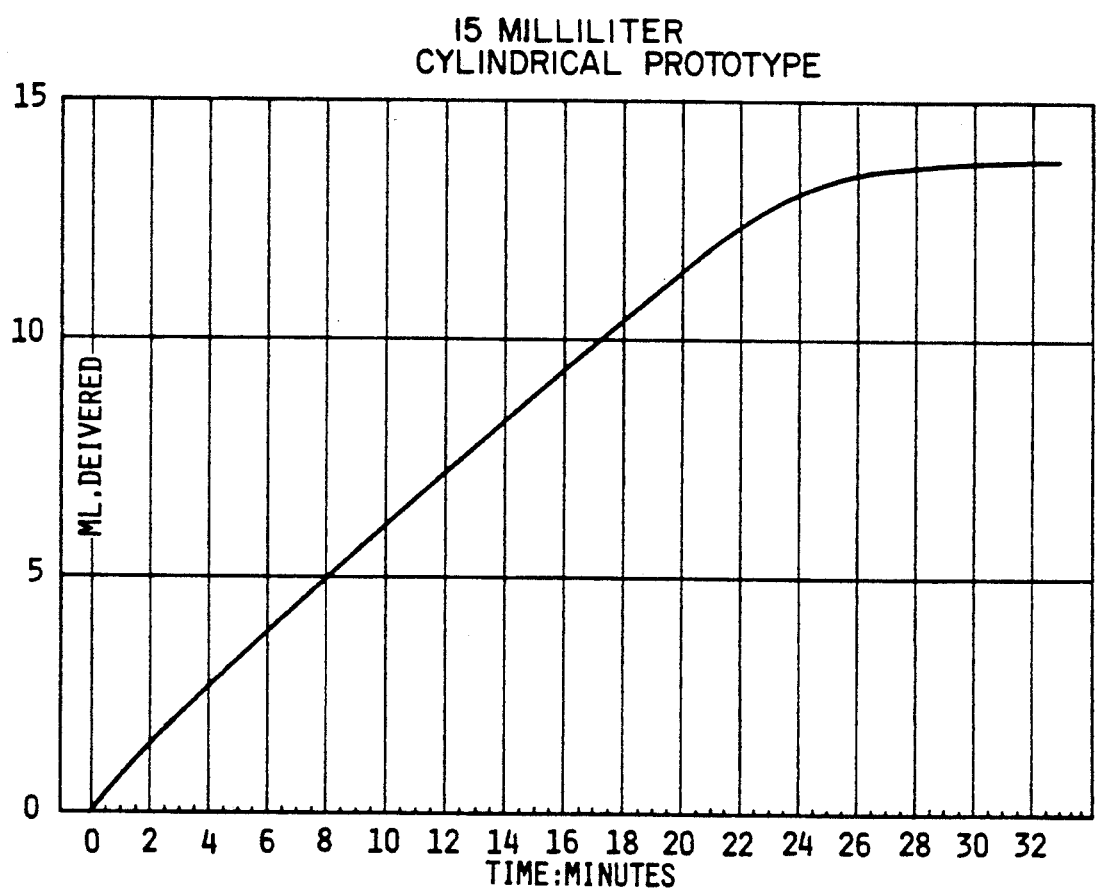
FIG. 9A shows a flow curve from an embodiment of the present invention incorporating the deformable member of FIG. 1 in the cylindrical housing of FIG. 8.
Figure 9B:
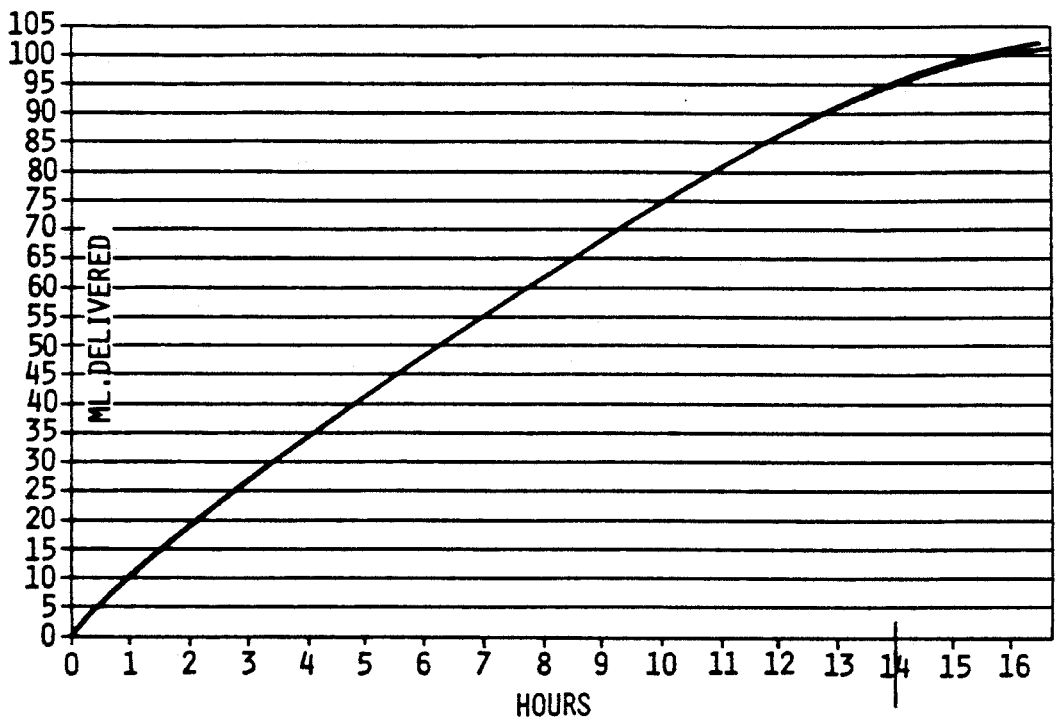
FIG. 9B shows a flow curve from the embodiment of the present invention illustrated in FIG. 10.
Figure 9C:
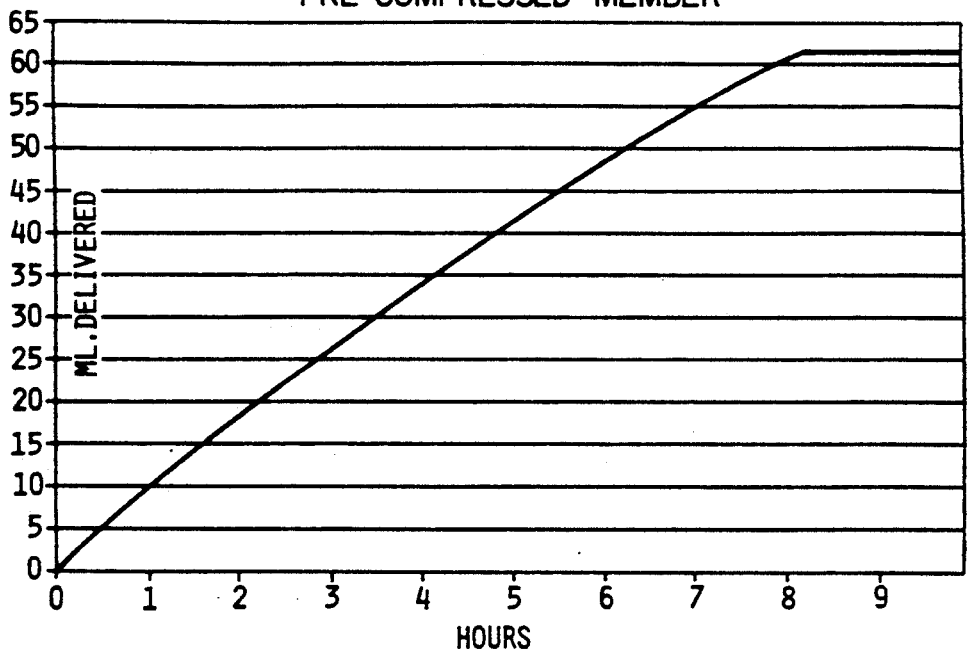
FIG. 9C shows a flow curve from the embodiment of the present invention illustrated in FIG. 10 but with a pre-loaded deformable member.

The infuser device of the present invention may be formed in a wide variety of geometric configurations and still provide for controlled discharge of fluid. For example, FIG. 9A illustrates the controlled discharge at a constant rate from a device utilizing a semi-spherical deformable member housed within a 15 milliliter capacity cylindrical housing such as that shown in FIG. 8. FIG. 9B illustrates the flow curve of a 105 milliliter capacity rectangular apparatus similar to that shown in FIG. 10, wherein the center of the deformable member is substantially rigid. FIG. 9C shows a flow curve from the rectangular device of FIG. 10 with the deformable member having been precompressed prior to the introduction of fluid. As illustrated by the similarity of these curves, the present invention is capable of providing controlled discharge for either large or small fluid volumes with such control being achievable in infusers incorporating various deformable member designs and housing configurations.

It will be appreciated that while the infuser of the present invention is capable of expelling fluid at a controlled rate, which may be either constant or variable, additional control over the rate of discharge may be achieved by restricting the rate of flow downstream from the infuser inlet/outlet means 28. As will be readily recognized by those skilled in the art, suitable flow control means may be attached directly to the fluid inlet/outlet 28.

Figure 10:
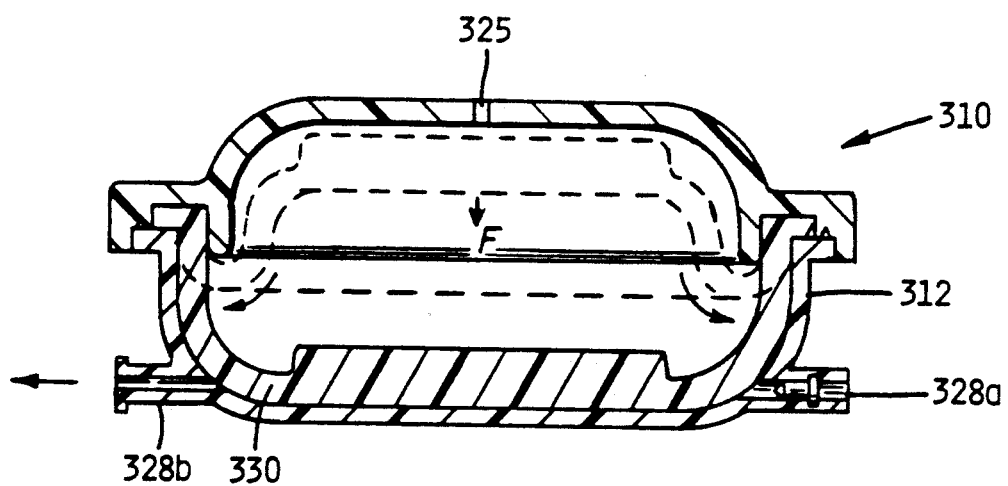
FIG. 10 is a cross section of a rectangular embodiment of the present invention having separate inlet and outlet ports.

FIG. 10 illustrates an embodiment of the invention 310 in which the housing 312 includes separate inlet means 328a and outlet means 328b. As described below, flow control means in the form of a fluid administration set may be connected to outlet means 328b. Similar flow control means may, of course, also be connected to the inlet/outlet means of any embodiment of the present invention.

Figure 11A:
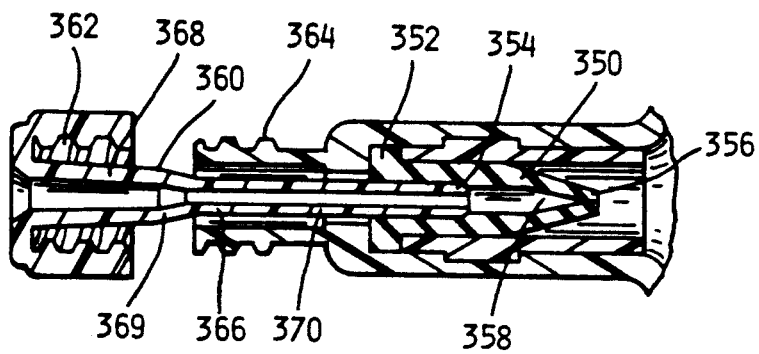
FIGS. 11A and 11B are sectional views of a valve arrangement and an unlocking mechanism for the inlet/outlet means of the drug infuser of the present invention.
Figure 11B:
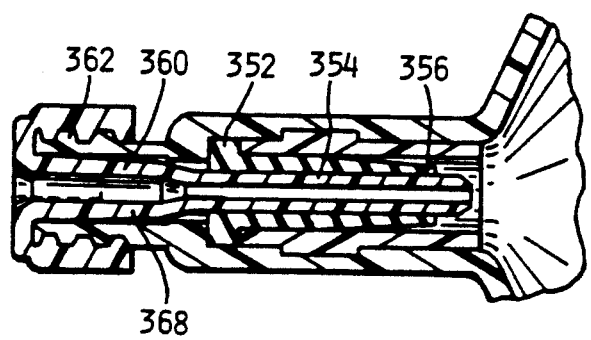

In accordance with a preferred embodiment, the inlet/outlet means 28 of the present invention includes an elastomeric duckbill valve means 350 as shown in greater detail in FIGS. 11A and 11B. The valve 350 is normally closed, as shown in FIG. 11A to prevent fluid from leaking out of fluid stroage means 35. The valve 350 generally comprises an end flange portion 352, an elongated central portion 354, which terminates in a tapered end portion 356, and a lumen 358 which extends from the flange portion 352 to the tapered end portion 356. The tapered end portion 356 provides a seal by which the valve 350 is normally closed.

In keeping with another preferred embodiment of the present invention, a combination male luer 360 and fluid administration set is provided for opening the duck bill valve 350 and further controlling the rate at which the fluid is delivered by the apparatus. As best seen in FIG. 11A, male luer 360 includes a threaded end portion 362 for threadingly engaging a corresponding threaded portion 364 of inlet/outlet means 28. Male luer 360 includes an elongated tube 366 having a portion 368 of one diameter which tapers at 369 to an elongated portion 370 having a smaller diameter than the first diameter portion 368. The elongated portion 370 of male luer 360 has a diameter such that the elongated portion 370 can press fit into the lumen 358 of duck bill valve 350 to form a seal between the smaller diameter portion 370 of male luer 360 and the elastomeric material of the duck bill valve 350. As illustrated in FIG. 11B, when the smaller diameter portion 370 of male luer 360 is advanced into valve 350 sufficiently, the tapered portion 356 of duck bill valve 350 is opened, thereby permitting fluid to flow into the lumen 358 of male luer 360.

Figure 11C:
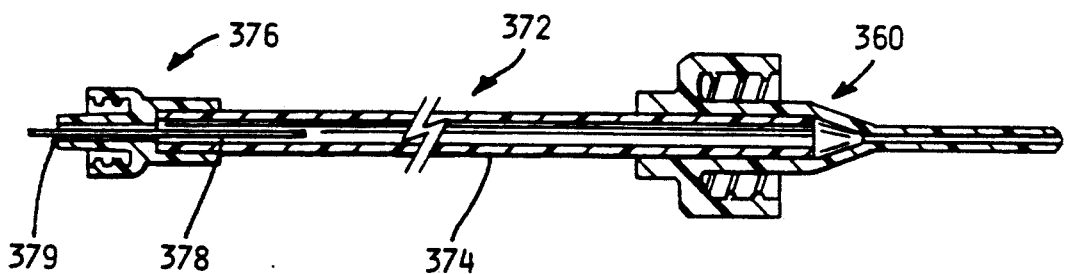
FIG. 11C is a cross section of a flow controlling fluid administration set adaptable to the inlet/outlet means of the drug infuser of the present invention.

At the threaded end 362 of the male luer 360 there is provided a fluid administration set 372 a preferred embodiment of which is illustrated in FIG. 11C. As illustrated, the fluid administration set 372 includes a length of tubing 374 disposed between male luer 360 and a female luer fitting 376. In the preferred embodiment, the tubing will be composed of extruded vinyl, although alternative biocompatible materials could be utilized if so desired. As illustrated in FIG. 11C, a length of polyimide or other acceptable tubing 378 is inserted into the end of the vinyl tubing 374. A sealant such as epoxy or ultra violet light curing adhesive is then applied to the open end of the female luer fitting 376 to form a seal 379 between female fitting 376 and polyimide tubing 378.

The seal 379 thus forces all fluid to pass through the polyimide tubing. Accordingly, as will be appreciated by those skilled in the art, the ultimate flow rate and discharge pressure of the fluid exiting the infuser apparatus may be controlled by adjustment of the length and diameter of the polyimide tubing 378.

The ability to accurately control the discharge pressure of the fluid expelled from each individual infuser, through selection of the deformable member and the flow control means, permits multiple infusers to be coupled together to effect a staged discharge of the fluids contained therein. One embodiment of such a staged configuration using two infusers feeding a common header line is illustrated in FIG. 12.

Figure 12:
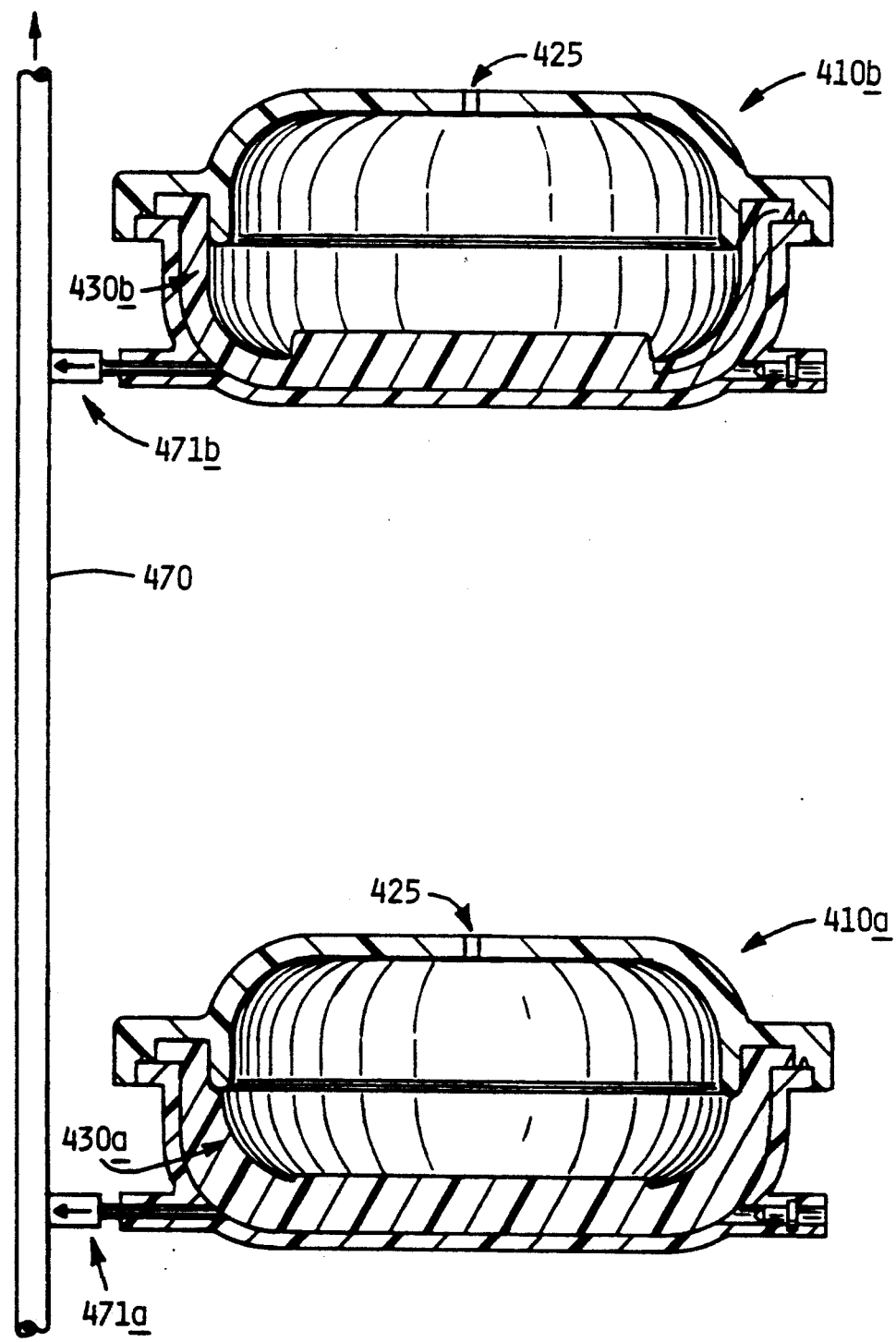
FIG. 12 is a representative view of a flow system utilizing a plurality of drug infusers according to the present invention.

In the embodiment shown in FIG. 12, the infusers 410a and 410b are identical in all respects except for the thickness, and hence the rigidity, of the respective deformable members 430a and 430b. Since the thickness of the deformable member 430a is greater than that of member 430b, the discharge pressure of the fluid expelled by infuser 410a will be greater than the discharge pressure of the fluid expelled by infuser 410b. Accordingly, the fluid housed in infuser 410b will be unable to overcome the pressure differential and flow into the header 470 until the discharge for infuser 410a is substantially complete. Backflow of the fluid discharged from one infuser into the other is prevented by means of one-way valves 471a and 471b.

While the embodiment illustrated in FIG. 12 utilizes only two infusers, it will be readily appreciated that a staged discharge system may utilize multiple infusers. Likewise, a staged system is not limited to a configuration in which one infuser is completely emptied before discharge from subsequent infusers is initiated. Rather, infusers having various combinations of deformable members and flow control means may be coupled via common header lines to effect a virtually infinite variety of flow combinations.

The present invention thus provides a simple fluid infusing device capable of delivering drugs or other fluids at a controlled rate substantially through the relief of the internal bending strains of a deformable member. It can be used either with or without additional flow control means and may be used in conjunction with other infusing devices to create an effective fluid delivery system.

I claim as my invention:

1. An infuser apparatus for the delivery of a fluid at a controlled rate of flow comprising in combination:
a housing having a first portion and a second portion, said housing defining an inner chamber, said inner chamber having a first and a second inner surface;
a deformable member disposed in said inner chamber, said deformable member normally disposed in contacting relation with said first inner surface when said infuser is unfilled, inlet means for introducing fluid into said inner chamber in between said deformable member and said first inner surface, said deformable member and said first inner surface defining a fluid storage means, said fluid storage means including fluid outlet means, said deformable member bending away from said first inner surface as fluid is introduced into said fluid storage means, said deformable member having bending strain recovery properties to exert a pressure force against fluid in said fluid storage means, said pressure force causing fluid contained in said inner fluid storage means to be expelled at a controlled rate as said deformable member returns by relief of internal bending strains to its original disposition against said first inner surface.

2. An apparatus according to claim 1 wherein the fluid contained in said inner fluid storage means is expelled at a substantially constant rate and under a substantially constant pressure.

3. An apparatus according to claim 1 wherein said housing comprises a thermoplastic material.

4. An apparatus according to claim 3 wherein said thermoplastic material is selected from the group consisting of acrylics, polypropylenes and polycarbonates.

5. An apparatus according to claim 1 wherein said deformable member comprises a heat cured elastomeric material.

6. An apparatus according to claim 5 wherein said elastomeric material is selected from the group consisting of synthetic and natural rubber.

7. An apparatus according to claim 1 wherein said deformable member comprises a non-heat cured elastomer.

8. An apparatus according to claim 7 wherein said deformable member comprises a thermoplastic material.

9. An apparatus according to claim 1 wherein said deformable member and said first inner surface are of a semi-spherical geometry.

10. An apparatus according to claim 1 wherein said deformable member and said first inner surface are of a substantially rectangular geometry.

11. An apparatus according to claim 1, wherein said housing is of a substantially cylindrical geometry.

12. An apparatus according to claim 1 wherein the perimeter of said deformable member is secured between said first and second portions of said housing.

13. An apparatus according to claim 1 wherein said inner chamber includes ventilation means in communication with the atmosphere.

14. An apparatus according to claim 1 wherein the deformable member comprises a ribbed surface, said ribbed surface having raised ribs of higher rigidity and depressed areas of lower rigidity.

15. An apparatus according to claim 1 wherein barrier means is disposed between said deformable member and said first inner surface.

16. An apparatus according to claim 1 wherein the center of said deformable member is substantially rigid.

17. An apparatus according to claim 1 wherein said deformable member retians preloaded compressive stresses upon returning to normal contacting relation with said first inner surface.

18. The apparatus according to claim 1 wherein said fluid outlet means includes valve means.

19. An apparatus according to claim 18 wherein said apparatus includes a fluid administration set in communication with said fluid outlet means, said fluid administration set comprising means for further controlling the rate of fluid flow from said inner chamber in response to the return of the deformable member to contacting relation with said first inner surface.

20. The apparatus of claim 19 wherein said fluid administration set includes luer means for opening said valve means, said luer means comprising a first elongated tubular section having a first diameter and a second elongated tubular section having a second diameter, the first diameter of said tubular section being greater than the second diameter of said second elongated tubular section, and a tapered section connecting said first elongated tubular section to said second elongated tubular section, said second elongated tubular section being sufficiently long and having a diameter such that said luer means is capable of press fitting into said valve means to form a seal between said second elongated section and said valve means prior to said valve means being opened sufficiently to permit fluid to flow therethrough.

21. The apparatus of claim 18 wherein said valve means is a duck bill valve.

22. An apparatus according to claim 19 wherein said fluid administration set is detachable.

23. An infuser apparatus for the delivery of a fluid at a controlled varying rate of flow comprising in combination:

a housing having a first portion and a second portion, said housing defining an inner chamber, said inner chamber having a first and a second inner surface;

a deformable member disposed in said inner chamber and having sections of relatively higher rigidity and sections of relatively lower rigidity as measured across the surface of said deformable member, said deformable member normally disposed in contacting relation with said first inner surface when said infuser if unfilled, inlet means for introducing fluid into said inner chamber in between said deformable member and said first inner surface, said deformable member and said first inner surface defining a fluid storage means, said inner fluid storage means including fluid outlet means, said deformable member bending away from said first inner surface as fluid is introduced into said fluid storage means, said deformable member having bending strain recovery properties to exert a pressure force against fluid in said fluid storage means, said pressure force causing fluid contained in said inner fluid storage means to be expelled at a controlled rate as said deformable member returns by relief of internal bending strains to its original disposition against said first inner surface.

24. An apparatus according to claim wherein said deformable member comprises a heat cured elastomeric material.

25. An apparatus according to claim 24 wherein said elastomeric material is selected from the group consisting of synthetic and natural rubber.

26. An apparatus according to claim 23 wherein said deformable member comprises a non-heat cured elastomer.

27. An apparatus according to claim 26 wherein said deformable member comprises a thermoplastic material.

28. An apparatus according to claim 23 wherein said housing comprises a thermoplastic material.

29. An apparatus according to claim 28 wherein said thermoplastic material is selected from the group consisting of acrylics, polypropylenes and polycarbonates.

30. An apparatus according to claim 23 wherein said deformable member and said first inner surface are of a semi-spherical geometry.

31. An apparatus according to claim 23 wherein said deformable member and said first inner surface are of a substantially rectangular geometry.

32. An apparatus according to claim 23, wherein said housing is of a substantially cylindrical geometry.

33. An apparatus according to claim 23 wherein the perimeter of said deformable member is secured between said first and second portions of said housing.

34. An apparatus according to claim 23 wherein said inner chamber includes ventilation means in communication with the atmosphere.

35. An apparatus according to claim 23 wherein the deformable member comprises a ribbed surface, said ribbed surface having raised ribs of higher rigidity and depressed areas of lower rigidity.

36. An apparatus according to claim 23, wherein barrier means are disposed between said deformable member and the first inner surface.

37. An apparatus according to claim 23 wherein the center of said deformable member is substantially rigid.

38. An apparatus according to claim 23 wherein said deformable member retains preloaded compressive stresses upon returning to normal contacting relation with said first inner surface.

39. The apparatus according to claim 23 wherein said fluid outlet means includes valve means.

40. The apparatus according to claim 39 wherein said apparatus includes a fluid administration set in communication with said fluid outlet means, said fluid administration set comprising means for further controlling the rate of fluid flow from said inner chamber in response to the return of the deformable member to contacting relation with said first inner surface.

41. The apparatus according to claim 40 wherein said fluid administration set includes luer means for opening said valve means, said luer means comprising a first elongated tubular section having a first diameter and a second elongated tubular section having a second diameter, the first diameter of said tubular section being greater than the second diameter of said second elongated tubular section, and a tapered section connecting said first elongated tubular section to said second elongated tubular section, said second elongated tubular section being sufficiently long and having a diameter such that said luer means is capable of press fitting into said valve means to form a seal between said second elongated section and said valve means prior to said valve means being opened sufficiently to permit fluid to flow therethrough.

42. The apparatus of claim 39 wherein said valve means is a duck bill valve.

43. A system for the delivery of a plurality of fluids at staged intervals comprising:

a plurality of infuser devices;

each infuser comprising in combination, a housing having a first portion and a second portion, said housing defining an inner chamber having a first inner surface and a second inner surface, a deformable member disposed in said inner chamber, said deformable member normally disposed in contacting relation with said first inner surface when said infuser is unfilled, inlet means for introducing fluid into said inner chamber in between said deformable member and said first inner surface, said deformable member and said first inner surface defining a fluid storage means, said fluid storage means including fluid outlet means, said deformable member bending away from said first inner surface as fluid is introduced into said fluid storage means, said deformable member having bending strain recover properties to exert a pressure force against fluid in said fluid storage means, said pressure force causing fluid contained in said inner fluid storage means to be expelled as said deformable member returns by relief of internal bending strain to said normal disposition against said first inner surface, and connecting means whereby the fluid outlet means of the infuser devices may be coupled together.

44. A system according to claim 43 wherein said recovery properties for each deformable member are such that said pressure force produced is quantitatively different for at least two infusers.

45. A system according to claim 43 wherein at least one infuser contains a deformable member having sections of relatively higher rigidity and sections of relatively lower rigidity as measured across the surface of said deformable member.

46. A system according to claim 43 wherein at least two infusers include deformable members having geometric differences.

47. A system according to claim 43 wherein at least one infuser includes conduit means in communication with said fluid outlet means, said conduit means comprising means for restricting the rate of fluid flow from said inner chamber in response to the return of the deformable member to contacting relation with said first inner surface.

* * * * *

UNITED STATES PATENT AND TRADEMARK OFFICE
CERTIFICATE OF CORRECTION

PATENT NO. : 5,306,257
DATED : April 26, 1994
INVENTOR(S) : Zdeb

It is certified that error appears in the above-indentified patent and that said Letters Patent is hereby corrected as shown below:

Column 11, claim 17, line 2, delete "retinas" and substitute therefor -- retains --;

Column 12, claim 24, line 1, delete "claim wherein" and substitute therefor -- claim 23 wherein --;

Signed and Sealed this

Twenty-seventh Day of September, 1994

Attest:

BRUCE LEHMAN

Attesting Officer    Commissioner of Patents and Trademarks